(12) United States Patent
Lee et al.

(10) Patent No.: US 7,847,134 B2
(45) Date of Patent: Dec. 7, 2010

(54) PROCESS OF PRODUCING MONOHYDRIC ALCOHOLS FROM MONOCARBOXYLIC ACIDS OR DERIVATIVES THEREOF

(75) Inventors: Jung Ho Lee, Daejeon (KR); Jong San Chang, Daejeon (KR); Young Kyu Hwang, Daejeon (KR); Hyun Kwan Shin, Daejeon (KR); Kwang Myung Cho, Daejeon (KR); Bong Keun Song, Daejeon (KR); Yong Hwan Kim, Daejeon (KR)

(73) Assignee: Korea Research Institute of Chemical Technology, Taejeon-Si (KR)

( * ) Notice: Subject to any disclaimer, the term of this patent is extended or adjusted under 35 U.S.C. 154(b) by 0 days.

(21) Appl. No.: 12/594,025

(22) PCT Filed: Feb. 27, 2009

(86) PCT No.: PCT/KR2009/000963

§ 371 (c)(1),
(2), (4) Date: Sep. 30, 2009

(87) PCT Pub. No.: WO2009/110698

PCT Pub. Date: Sep. 11, 2009

(65) Prior Publication Data

US 2010/0113843 A1      May 6, 2010

(30) Foreign Application Priority Data

Mar. 6, 2008    (KR) .................. 10-2008-0021115

(51) Int. Cl.
C07C 29/147    (2006.01)

(52) U.S. Cl. .................................... 568/885

(58) Field of Classification Search .................. 568/885
See application file for complete search history.

(56) References Cited

U.S. PATENT DOCUMENTS

| 4,443,639 | A | 4/1984 | Pesa et al. |
| 5,334,779 | A | 8/1994 | Kuo |
| 5,414,159 | A | 5/1995 | Appleton et al. |
| 5,981,769 | A | 11/1999 | Baur et al. |
| 6,077,964 | A | 6/2000 | Tuck et al. |
| 6,100,410 | A | 8/2000 | Tuck et al. |
| 6,495,730 | B1 | 12/2002 | Konishi et al. |

*Primary Examiner*—Sikarl A Witherspoon
(74) *Attorney, Agent, or Firm*—Lucas & Mercanti, LLP

(57) ABSTRACT

Disclosed herein is a method for producing monohydric alcohols from monocarboxylic acids or derivatives thereof using a catalyst comprising ruthenium (Ru) and tin (Sn) using zinc oxide (ZnO) as both a catalyst support and an active promoter; a catalyst prepared by adding an inorganic binder such as silica, alumina or titania in a limited range to the catalyst comprising the above components in order to impart a shaping ability to the catalyst; or, a modified catalyst reformed by adding at least one reducing component selected from the group consisting of Co, Ni, Cu, Ag, Rh, Pd, Re, Ir, and Pt to the catalyst in order to improve the reducing ability of the catalyst. By using such catalysts, the method according to the present invention is advantageous in that the monohydric alcohols can be prepared in high yield regardless of whether the monocarboxylic acids contain water or not, the monohydric alcohols can be economically prepared because the catalysts can be operated under mild reaction conditions and also exhibits high selectivity and productivity compared to conventional catalysts, and the catalysts have excellent long-term reaction stability so as to be advantageous for industrial applications.

10 Claims, No Drawings

PROCESS OF PRODUCING MONOHYDRIC ALCOHOLS FROM MONOCARBOXYLIC ACIDS OR DERIVATIVES THEREOF

CROSS-REFERENCE TO RELATED APPLICATIONS

This application is a 371 of PCT/KR2009/000963 filed on Feb. 27, 2009, which claims the benefit of Korean Patent Application No. 10-2008-0021115 filed on Mar. 6, 2008, the contents of each of which are incorporated herein by reference.

BACKGROUND OF THE INVENTION

1. Field of the Invention

The present invention relates to a method for producing monohydric alcohols from a monocarboxylic acid and, more particularly, to a method for producing a monohydric alcohol from a monocarboxylic acid using a hydrogenation catalyst which can directly hydrogenate the monocarboxylic acid in the gas phase regardless of whether or not the monocarboxylic acid contains water.

2. Description of the Related Art

To cope with the shortage of petroleum resources and solve global environmental problems, many researches have been conducted to develop an alternative energy source to petroleum used as an automobile fuel, and biofuels such as bioethanol and biodiesel are currently used as a petroleum-alternative transportation fuel in some countries. Meanwhile, biobutanol has advantages in that it causes no corrosion of automobiles and has a high boiling point, as compared to bioethanol. Further, biobutanol has advantages in that it can be directly used in an automobile system originally designed for using petroleum fuel without special modification of the automobile system, and it has higher fuel efficiency per volume than bioethanol. However, biobutanol preparation processes have a lower yield and productivity than bioethanol preparation processes, and a bio-process capable of economically preparing biobutanol has not yet been developed.

Accordingly, a new technology to utilize n-butyric acid from biomass as an intermediate of producing butanol is being considered as an alternative of the biobutanol processes. It is based on the bio-chemical composite technology, in which n-butanol is synthesized by preparing n-butyric acid from biomass through a bioprocess like fermentation and then reducing the n-butyric acid through a thermocatalytic process.

In petrochemical industry, n-butanol has been so far prepared in a large quantity through a hydroformylation reaction of propylene followed by a hydrogenation reaction. In chemical industry, n-butanol is widely utilized as a chemical solvent, a plasticizer, a reactant for butylamine, and the like.

It is a chemically easy reaction to prepare monohydric alcohols such as n-butanol by a reduction reaction of monocarboxylic acids such as n-butyric acid. However, an expensive strong reducing agent such as lithium aluminum hydride ($LiAlH_4$) is used in the above-described chemical reaction, and thus the reduction reaction using such an expensive reducing agent is not suitable for mass production of commercially important monohydric alcohols such as n-butanol.

Meanwhile, in order to produce monohydric alcohols at the industrial scale, it has been used a hydrogenation reaction using hydrogen as a reducing agent on a hydrogenation catalyst. However, such a hydrogenation reaction cannot be generally applied to the direct hydrogenation of monocarboxylic acids. This is because conventional hydrogenation catalysts are often dissolved in a carboxylic acid which is a reactant and thus its catalytic activity is not maintained for a long period of time in the presence of the carboxylic acid, or because components of hydrogenation catalysts cause the decarboxylation of the carboxylic acid to lower selectivity in the direct hydrogenation reaction of the carboxylic acid.

Therefore, most hydrogenation processes of monocarboxylic acids have been performed by a method involving two steps of esterifying carboxylic acid with methanol or ethanol to obtain an esterified compound and then hydrogenating the obtained esterified compound to prepare a monohydric alcohol. For example, 1,4-butanediol is prepared by hydrogenating an esterified compound obtained from maleic acid or maleic anhydride with methanol or ethanol [U.S. Pat. Nos. 6,100,410, 6,077,964, 5,981,769, 5,414,159, and 5,334,779].

However, since these processes additionally includes the esterification reaction process and processes of recovering and purifying alcohols used in the esterification reaction in the hydrogenation of carboxylic acid, and processes for recovering and purifying unreacted esterified compounds remaining after the hydrogenation reaction, the reaction processes become complicated and production costs are disadvantageous.

In order to solve the above-mentioned problems, many researches have been conducted to simplify reaction processes for producing monohydric alcohols.

For example, U.S. Pat. No. 6,495,730 and cited references therein disclose a hydrogenating catalyst system for preparing 1,4-butanediol by directly hydrogenating maleic acid or succinic acid under a reaction condition in which an excessive amount of water is supplied as compared with the amount of carboxylic acid [wherein, the hydrogenating catalyst system includes ruthenium-tin/activated carbon; ruthenium-iron oxides; ruthenium-tin/titania or alumina; ruthenium-tin and a component selected from alkali metals and alkaline earth metals; a component selected from tin-ruthenium, platinum and rhodium; and, ruthenium-tin-platinum/activated carbon].

Further, U.S. Pat. No. 4,443,639 discloses a ruthenium-based catalyst, $ARuDEO_x$ (A=Zn, Cd, Ni and mixtures thereof, and E=Fe, Cu, Rh, Pd, Os, Ir, Pt and mixtures thereof) as a hydrogenation catalyst of n-butyric acid, wherein it is exemplified that n-butanol is obtained in the presence of water and n-butylbutyrate is obtained in the absence of water.

However, these conventional technologies are problematic in that, since an excessive amount of water is used to prepare monohydric alcohols from carboxylic acids (for example, U.S. Pat. No. 4,443,639: 10 wt % of aqueous acid is used), an amount of generated waste water and energy consumption are high and productivity is low (for example, LHSV: 0.1 $hr^{-1}$ or less), and a high pressure of 60 atms or more is required.

For this reason, in order to produce monohydric alcohols at the industrial scale through the hydrogenation of monocarboxylic acids, there have been demands for developing an economical preparation technology.

Hence, the present inventors have conducted many experiments to solve the above-described problems of the conventional technologies using ruthenium-based catalysts to hydrogenate carboxylic acids, in which the problems are that a high reaction pressure is required; an excessive amount of water should be simultaneously supplied to reactants; industrial application is difficult due to low productivity, and the like. As a result, they have found that activity and selectivity of carboxylic acid hydrogenation reaction are remarkably improved in case of using a catalyst which contains a proper concentration of ruthenium (Ru) and is modified with tin (Sn) using zinc oxide (ZnO) as both a catalyst support and an active promoter, and that monohydric alcohols can be efficiently produced by hydrogenating monocarboxylic acids in the gas phase under the presence of the catalyst using a fixed-bed reaction. Based on these findings, the present invention has been completed.

SUMMARY OF THE INVENTION

Accordingly, the present invention has been made to solve the above conventional problems, and an object of the present invention is to provide a method for producing a monohydric alcohol by direct hydrogenation of a monocarboxylic acid regardless of the content of water in the reaction mixture. In this method, monohydric alcohols can be continuously produced over a long period of time with high space yield and high selectivity even under mild reaction conditions using a hydrogenation catalyst having excellent thermal stability, chemical stability and reaction activity.

In order to accomplish the above object, the present invention provides a method for producing a monohydric alcohol, including direct hydrogenation of a monocarboxylic acid with hydrogen in the presence of a catalyst having a composition including Ru, Sn and Zn as an essential component, represented by the following Chemical Formula 1:

$$Ru(a)Sn(b)Zn(d)O_x \quad \text{[Chemical Formula 1]}$$

wherein, (a), (b), (d) and x is defined in the present specification.

DESCRIPTION OF THE PREFERRED EMBODIMENTS

Hereinafter, preferred embodiments of the present invention will be described in detail.

The present invention provides a method for producing a monohydric alcohols, including direct hydrogenation of a monocarboxylic acid or a derivative thereof with hydrogen in the presence of a catalyst having a composition including Ru, Sn and Zn as an essential component, represented by the following Chemical Formula 1:

$$Ru(a)Sn(b)Zn(d)O_x \quad \text{[Chemical Formula 1]}$$

wherein, each of (a), (b) and (d) represents an atomic ratio of each component satisfying the relation that (a) is 1~20, preferably 2~10, and (b) is 1~40, preferably, 2~20 when (d) is 100; and, x is the number of oxygen atoms, which is determined according to the atomic valences and composition ratios of other components.

Also, as represented by the following Chemical Formula 2, the present invention provides a method for producing a monohydric alcohol, including direct hydrogenation of a monocarboxylic acid with hydrogen in the presence of a catalyst prepared by adding components A which is one or more members selected from the group consisting of Co, Ni, Cu, Ag, Rh, Pd, Re, Ir and Pt to the catalyst represented by Chemical Formula 1:

$$Ru(a)Sn(b)A(c)Zn(d)O_x \quad \text{[Chemical Formula 2]}$$

wherein,

A is one or more members selected from the group consisting of Co, Ni, Cu, Ag, Rh, Pd, Re, Ir and Pt;

each of (a), (b), (c) and (d) is an atomic ratio of each component satisfying the relation that (a) is 1~20, preferably, 2~10, (b) is 1~40, preferably, 2~20, and (c) is more than 0 to 20 when (d) is 100; and x is the number of oxygen atoms, which is determined by the atomic valences and composition ratios of other components.

Further, as represented by the following Chemical Formula 3, the present invention provides a method for producing a monohydric alcohol, including direct hydrogenation of a monocarboxylic acid with hydrogen in the presence of a catalyst which is prepared by adding components B which is one or more members selected from the group consisting of Si, Ti and Al to the catalyst represented by Chemical Formula 2:

$$Ru(a)Sn(b)A(c)Zn(d)B(e)O_x \quad \text{[Chemical Formula 3]}$$

wherein

A represents one or more members selected from the group consisting of Co, Ni, Cu, Ag, Rh, Pd, Re, Ir and Pt;

B represents one or more members selected from the group consisting of Si, Ti and Al;

each of (a), (b), (c), (d) and (e) represents an atomic ratio of each component satisfying the relation that (a) is 1~20, preferably 2~10, (b) is 1~40, preferably, 2~20, (c) is more than 0 to 20, preferably more than 0 to 10, (d) is 50 or more, preferably, 80~100, and (e) is more than 0 to 50, preferably more than 0 to 20 when (d)+(e) is 100; and, x is the number of oxygen atoms, which is determined by the atomic valences and composition ratios of other components.

That is, the catalyst used in the method of producing a monohydric alcohol according to the present invention may be a catalyst containing ruthenium (Ru) and tin (Sn) components using a zinc oxide (ZnO) as both a catalyst support and an active promoter; a catalyst prepared by adding an inorganic binder such as silica, alumina or titania in a limited range to the above catalyst in order to impart formability to the catalyst containing the above components; or, a catalyst reformed by adding at least one reducing component selected from the group consisting of Co, Ni, Cu, Ag, Rh, Pd, Re, Ir, and Pt to the catalyst in order to improve the reduction ability of the catalyst.

As for the catalyst used in the method for producing a monohydric alcohol according to the present invention, ruthenium (Ru) is a core element exhibiting hydrogenation activity. When the composition ratio of support components containing zinc (Zn) based on the number of atoms of the support components is 100, the composition ratio of ruthenium (Ru) may be 1~20, preferably 2~10. When the composition ratio of ruthenium (Ru) is less than these ranges, the hydrogenation activity of the catalyst is low. On the other hand, the Ru composition greater more than these ranges is not desirable in view of a high price of ruthenium (Ru) compared to an increase in the hydrogenation activity of the catalyst.

Tin (Sn) component serves as an activity promoter and a stabilizer of ruthenium (Ru) component. The composition ratio of Sn may be 1~40, preferably 2~20. When the composition ratio of tin (Sn) is less than or more than these ranges, tin (Sn) have no effect on improving ruthenium (Ru).

Zinc (Zn), serving as both a catalyst support and an active promoter, exists in the form of an oxide such as ZnO, and ZnO independently performs a role as a catalyst support and even an active promoter sufficiently. However, when an extrusion molding method is applied to use the catalyst according to the present invention as an industrial catalyst, an inorganic binder may be added if necessary in order to impart strength to the molded catalyst material. As the inorganic binder B, one or more members selected from the group consisting of silica, alumina and titania (titanium dioxide) may be added to the catalyst.

In this case, the amount of the inorganic binder B added to the catalyst may be 50 or less (for example, when B is 50:$Zn_{50}$ $B_{50}$), preferably 20 or less. When the amount of the added inorganic binder B is more than these ranges, the activity of the catalyst is deteriorated, and the selectivity of the catalyst is decreased due to an increase in the dehydrating ability of the catalyst.

Meanwhile, although ruthenium (Ru) component independently exhibits sufficient catalytic activity, the catalyst may further include component A which is one or more members selected from the group consisting of Co, Ni, Cu, Ag, Rh, Pd, Re, Ir, and Pt which have been well known as a reducing catalyst component in order to improve the reducing ability of the catalyst. In this case, the component A may be added to the catalyst such that the ratio of the component A with respect to ruthenium (Ru) component is 0.5 or less.

When the amount of the component A added is more than the above ranges, the activity of the catalyst is decreased due to the formation of alloys or mixtures of the component A with ruthenium (Ru), or the selectivity of the catalyst is decreased due to decarboxylation.

The catalyst of Chemical Formula 1, used in the method for producing monohydric alcohols according to the present invention, may be prepared by impregnating a ZnO-containing support with Ru, Sn and the like; by preparing Sn and Zn oxide particles (in this case, they may include other inorganic support components and may be prepared by a coprecipitation or impregnation method) and then impregnating them with reducing metal components including Ru; by simultaneously coprecipitating all catalyst components; or, by a sol-gel method.

Water-soluble salts used to prepare the catalyst according to the present invention may include chlorides, nitrates and the like. A coprecipitating agent (or a precipitating agent) may include any one selected from the group consisting of ammonia, sodium hydroxide, sodium carbonate, and sodium bicarbonate. The molded catalyst materials may have various shapes, but not limited to, such as a sphere, a rod, a ring and the like, and may be prepared by any methods such as an extrusion molding method, a tabletting molding method, an impregnation method or the like, without limitation.

The catalyst of Chemical Formula 1, prepared by the above-described methods, undergoes a sintering process. The sintering process is generally conducted at a temperature of 300~800° C., preferably 350~600° C. under an air atmosphere.

Subsequently, the metal oxide-based catalyst of Chemical Formula 1 undergoes an activation process prior to performing the hydrogenation reaction of monocarboxylic acids. The activation process is conducted at a temperature of 200~600° C., preferably 250~400° C. using a mixed gas of $H_2$ and $N_2$.

Further, the monocarboxylic acid(s) used in the method for producing the monohydric alcohol(s) according to the present invention may include a monocarboxylic acid(s) of 1 to 10 carbon atoms, preferably a monocarboxylic acid(s) of 1 to 8 carbon atoms having a boiling point of 250° C. or lower, because the hydrogenation is necessarily conducted in the gaseous phase. The alkyl group part in the monocarboxylic acid(s) may be a linear or branched alkyl group. The monocarboxylic acid(s) of 1 to 8 carbon atoms are preferred. Specifically, the monocarboxylic acid(s) of 1 to 8 carbon atoms may include, linear or branched, formic acid, acetic acid, propanoic acid, butyric acid, pentanoic acid, hexanoic acid, heptanoic acid, octanoic acid, isomers thereof, and the like.

Further, the reactants used in the method for producing the monohydric alcohol(s) according to the present invention may include derivatives of the monocarboxylic acid(s). Such derivatives may include carboxylic anhydrides and carboxylic esters. The method for producing monohydric alcohols according to the present invention is very useful to prepare n-butanol from n-butyric acid or derivatives thereof such as anhydrides or esters thereof.

Conditions for the hydrogenation of the monocarboxylic acid(s) are as described below.

A temperature for the hydrogenation reaction is 150~400° C., preferably 170~300° C.; a pressure for the hydrogenation reaction is 0~50 atms, preferably 1~50 atms, more preferably 1~30 atms; the molar ratio of hydrogen ($H_2$) to monocarboxylic acid is 10~200:1, preferably 20~100:1; and the feed rate of monocarboxylic acid is 0.05~5 $hr^{-1}$, preferably 0.2~3 $hr^{-1}$.

The present invention is not restricted by the water-content ratio of the monocarboxylic acids.

In the hydrogenation of the monocarboxylic acids according to the above method, high activity is exhibited even when a pure monocarboxylic acid or water-containing monocarboxylic acid is used, high activity is exhibited even under a very low reaction pressure, and high productivity to sufficiently convert the reactants is exhibited even under a high space velocity.

Therefore, according to the method for producing the monohydric alcohol(s) from the monocarboxylic acid(s) according to the present invention, the monohydric alcohol(s) can be economically prepared because the catalyst can be operated under mild reaction conditions and exhibits high selectivity and high productivity compared to conventional catalysts, and the catalyst has excellent long-term reaction stability so as to be advantageously used for application to industrially production.

Hereinafter, the present invention will be described in more detail with reference to the following examples. However, it should be noted that the scope of the present invention is not limited thereto.

Example 1

(1-1) Preparation of a Catalyst Having a Composition of $Ru_{4.75}Sn_{8.07}Zn_{100}Ox$ A catalyst slurry solution was prepared through a coprecipitation process by simultaneously and dropwisely adding a solution containing 1.15 g of ruthenium chloride ($RuCl_3$, Ru 43.6 wt %), 1.901 g of tin chloride (II) ($SnCl_2.2H_2O$) and 31.07 g of zinc nitrate ($Zn(NO_3)_2.6H_2O$) dissolved in 300 ml deionized water and a sodium hydroxide solution at room temperature under rapid stirring. The final catalyst slurry solution was adjusted to have a pH of 7.2, and then slowly heated to be hydrothermally aged at a temperature of 80° C. for hours. Subsequently, the slurry solution containing hydrothermally-aged catalyst was cooled to room temperature, sufficiently washed with deionized water, and then filtered to obtain a catalyst cake. After the filtered catalyst cake was dried at a temperature of 120° C. for 10 hours. The dried catalyst cake was powdered and molded by a tabletting molding method, and then crushed and fractionated with 20~40 mesh size. The fractionated catalyst was sintered at a temperature of 450° C. for 6 hours under an air atmosphere.

(1-2) Activation of Catalyst

The calcined catalyst of 2.0 g was charged into a tubular reactor, and was then activated at a temperature of 280° C. for 12 hours with slowly heating it under flowing a mixed gas of $H_2$ and $N_2$.

(1-3) Hydrogenation Reaction of N-Butyric Acid

After the reduction activation of the catalyst, n-butyric acid was continuously reacted under the conditions of a reaction temperature of 250° C., a reaction pressure of 25 atms, a weight hour space velocity (WHSV) of 1.0 $hr^{-1}$ and a ratio of $H_2$/n-BA(molar ratio) of 35 to obtain a reaction product.

The reaction product was analyzed by gas chromatography (GC). As a result, after 100 hours, it was found that the conversion ratio of n-butyric acid was 99.9%, and the selectivity to n-butanol was 98.3%.

Example 2

The activity of the catalyst prepared in Example 1 was examined while changing reaction pressure. The reaction conditions of Example 2 except the reaction pressure were the same as those of Example 1. The results thereof are given in Table 1, in which it can be seen that the catalyst of the present invention exhibited high activity even at a low pressure of 5 atm or less.

TABLE 1

| Reaction pressure(atm) | Conversion ratio of n-butyric acid(%) | selectivity to n-butanol(%) |
|---|---|---|
| 20 | 99.9 | 98.6 |
| 10 | 99.9 | 98.3 |
| 7 | 99.9 | 98.4 |
| 2 | 99.6 | 98.5 |

*WHSV = 1.0 $hr^{-1}$, $H_2$/n-BA(m/m) = 35

Example 3

The same procedure as in Example 1 was performed, with the exception that n-butyric acid having a water content of 10 wt % was used and weight hour space velocity (WHSV) was 1.1 $hr^{-1}$.

As a result, it was found that the conversion ratio of n-butyric acid was 99.9%, and the selectivity to n-butanol was 98.2%.

Example 4

The continuous reaction was performed by the same procedure as in Example 1 at a reaction temperature of 250° C. and a reaction pressure of 7 atms for 1000 hours using the catalyst prepared in Example 1.

As a result, after 1000 hours, it was found that the conversion ratio of n-butyric acid was 99.9%, and the selectivity to n-butanol was 98.6%. Here, any change in activity of the catalyst was not observed at all.

Example 5

A catalyst having a composition of $Ru_{4.25}Sn_{8.07}Zn_{93}Si_7Ox$ was prepared using the same method as in Example 1. Colloidal silica (Ludox SM-30, manufactured by Grace Davison Co., Ltd.) having an average particle size of 7 nm, as $SiO_2$ used to prepare the catalyst, was diluted with deionized water having a pH of 9.5 and then used. After the preparation of catalyst slurry, the catalyst slurry was post-treated using the same method and conditions as in Example 1 to prepare the catalyst. The hydrogenation reaction of n-butyric acid was conducted using the catalyst prepared in Example 5 under the same conditions as in Example 1.

As a result, after 100 hours, it was found that the conversion ratio of n-butyric acid was 98.5%, the selectivity to n-butanol was 95.2%, and the selectivity to n-butyl butylate, which is an intermediate, was 3.5%.

Example 6

A catalyst having a composition of $Ru_{4.75}Sn_{8.07}Zn_{93}Ti_7O_x$ was prepared using the same method as in Examples 1 and 5. As a Ti component, titanium isopropoxide $(Ti(OiP)_4)$ was used by dissolving it in an isopropanol solution. After the preparation of catalyst slurry, the catalyst slurry was post-treated using the same method and conditions as in Example 1 to prepare the catalyst. Then, the hydrogenation reaction of n-butyric acid was conducted under the same conditions as in Example 1 using the catalyst prepared in Example 6.

As a result, after 100 hours, it was found that the conversion ratio of n-butyric acid was 97.7%, the selectivity of to n-butanol was 94.8%, and the selectivity to n-butylbutylate, which is an intermediate, was 3.9%.

Example 7

A catalyst having a composition of $Ru_{4.7}Cu_{0.5}Sn_{8.0}Zn_{100}O_x$ was prepared using the same method as in Example 1. As a Cu component, copper nitrate $(Cu(NO_3)_2.2.5H_2O)$ was dissolved with Ru and Sn compounds to prepare the catalyst. After the preparation of catalyst slurry, the catalyst slurry was post-treated using the same method and conditions as in Example 1 to prepare the catalyst. The hydrogenation reaction of n-butyric acid was conducted under the same conditions as in Example 1 using the catalyst prepared in Example 7.

As a result, after 1000 hours, it was found that the conversion ratio to n-butyric acid was 99.9%, and the selectivity to n-butanol was 98.9%.

Example 8

A catalyst having a composition of $Ru_{4.7}Co_{0.5}Sn_{8.0}Zn_{100}O_x$ was prepared using the same method as in Example 1. Here, the catalyst was prepared by dispersing zinc oxide (ZnO) powder in water and then a solution containing Ru, Co and Sn components dissolved in deionized water and a sodium hydroxide solution were simultaneously and dropwisely added into the ZnO-dispersed solution. In this case, $Co(NO_3)_2.6H_2O$ was used as a Co component. After the preparation of catalyst slurry, the catalyst slurry was post-treated using the same method and conditions as in Example 1 to prepare the catalyst. The activity of the catalyst prepared in Example 8 was examined under the same conditions as in Example 1.

As a result, after 100 hours, it was found that the conversion ratio of n-butyric acid was 99.9%, the selectivity to n-butanol was 95.2%, and the selectivity to n-butylbutylate, which is an intermediate, was 3.7%.

Example 9

A catalyst having a composition of $Ru_{4.7}Pt_{0.3}Re_{0.3}Sn_{8.0}Zn_{100}O_x$ was prepared using the same method as in Example 1, in which a slurry of an oxygen-containing mixture of Sn and Zn components was prepared by a coprecipitation method and then a solution containing Ru and Pt components dissolved in deionized water and a sodium hydroxide solution were simultaneously and dropwisely added into the slurry while stirring the slurry and adjusting pH of the slurry. In this case, $H_2PtCl_6 \cdot 6H_2O$ was used as a Pt component.

Thereafter, the catalyst was aged under a hydrothermal condition, washed and dried using the same method as in Example 1. Here, the dried catalyst cake was powdered and then impregnated with a solution containing $Re_2O_7$ dissolved in deionized water. Then, the drying, sintering, molding, crushing and fractionation of the impregnated catalyst cake was performed under the same conditions as in Example 1 to prepare the catalyst. The activity of the catalyst prepared in Example 9 was examined under the same conditions as in Example 1.

As a result, after 100 hours, it was found that the conversion ratio of n-butyric acid was 99.9% or more, and the selectivity to n-butanol was 98.4%.

As described above, according to the method for producing monohydric alcohols of the present invention, when a catalyst represented by Chemical Formula 1 is used, monohydric alcohols of 1 to 10 carbon atoms, preferably 1 to 8 carbon atoms, can be prepared in high yield regardless of whether or not monocarboxylic acids of 1 to 10 carbon atoms preferably 1 to 8 carbon atoms contain water. Further, since a catalyst used in the present invention can be operated under mild reaction conditions and exhibits high selectivity and productivity compared to conventional catalysts, monohydric alcohols can be economically prepared. Furthermore, since a catalyst used in the present invention has excellent long-term reaction stability, monohydric alcohols can be industrially prepared.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for producing monohydric alcohols, comprising direct hydrogenation of a $C_{1\sim10}$ monocarboxylic acid or a derivative thereof with hydrogen in the presence of a catalyst having a composition represented by the following Chemical Formula 1:

Ru(*a*)Sn(*b*)Zn(*d*)O*x*    [Chemical Formula 1]

wherein,
each of (a), (b) and (d) is an atomic ratio of each component satisfying the relation that (a) is 1 to 20 and (b) is 1 to 40 with respect to 100 of (d);
x is the number of oxygen atoms, which is determined according to the atomic valences and composition ratios of other components,
wherein the $C_{1\sim10}$ monocarboxylic acid or derivative thereof contains no water.

2. The method according to claim 1, wherein the catalyst further comprises component A which is one or more members selected from the group consisting of Co, Ni, Cu, Ag, Rh, Pd, Re, Ir and Pt, as represented by the following Chemical Formula 2:

Ru(*a*)Sn(*b*)A(*c*)Zn(*d*)O*x*    [Chemical Formula 2]

wherein,
A is one or more members selected from the group consisting of Co, Ni, Cu, Ag, Rh, Pd, Re, Ir and Pt;
each of (a), (b), (c) and (d) is an atomic ratio of each component satisfying the relation that (a) is 1 to 20, (b) is 1 to 40, and (c) is more than 0 to 20 with respect to 100 of (d); and,
x is the number of oxygen atoms, which is determined by the atomic valences and composition ratios of other components,
wherein the $C_{1\sim10}$ monocarboxylic acid or derivative thereof contains no water.

3. The method according to claim 2, wherein the catalyst further comprises component B which is one or more members selected from the group consisting of Si, Ti and Al, as represented by the following Chemical Formula 3:

Ru(*a*)Sn(*b*)A(*c*)Zn(*d*)B(*e*)O*x*    [Chemical Formula 3]

wherein
A is one or more members selected from the group consisting of Co, Ni, Cu, Ag, Rh, Pd, Re, Ir and Pt;
B is one or more members selected from the group consisting of Si, Ti and Al;
each of (a), (b), (c), (d) and (e) is an atomic ratio of each component satisfying the relation that (a) is 1 to 20, (b) is 1 to 40, (c) is more than 0 to 20, (d) is 50 or more and (e) is more than 0 to 50 with respect to 100 of (d)+(e) when (d)+(e); and,
x is the number of oxygen atoms, which is determined by the atomic valences and composition ratios of other components,
wherein the $C_{1\sim10}$ monocarboxylic acid or derivative thereof contains no water.

4. The method according to claim 1, wherein the catalyst is calcined at a temperature of 300 to 800° C. under an air atmosphere.

5. The method according to claim 1, wherein the catalyst is activated at a temperature of 200 to 600° C. using a mixed gas of $H_2$ and $N_2$ prior to performing the hydrogenation reaction of the $C_{1\sim10}$ monocarboxylic acid or derivative thereof.

6. The method according to claim 1, wherein the hydrogenation reaction is conducted by reducing the $C_{1\sim10}$ monocarboxylic acid or derivative thereof in the gas phase at a reaction temperature of 150 to 400° C. and a reaction pressure of 1 to 50 atms.

7. The method according to claim 1, wherein the molar ratio of hydrogen ($H_2$) to the $C_{1\sim10}$ monocarboxylic acid or derivative thereof in the hydrogenation reaction is 10 to 200:1.

8. The method according to claim 1, wherein the feed rate (LHSV) of the $C_{1\sim10}$ monocarboxylic acid or derivative thereof is 0.05 to 5 $hr^{-1}$ in the hydrogenation reaction.

9. The method according to claim 1, wherein the $C_{1\sim10}$ monocarboxylic acid is n-butyric acid, and the monohydric alcohol is n-butanol.

10. The method according to claim 1, wherein the derivative of the $C_{1\sim10}$ monocarboxylic acid is anhydrides or esters corresponding thereto.

* * * * *